United States Patent
Hansmann

(10) Patent No.: US 6,474,960 B1
(45) Date of Patent: Nov. 5, 2002

(54) RESPIRATOR RADIAL COMPRESSOR WITH REDUCED SOUND EMISSION

(75) Inventor: Hans-Ulrich Hansmann, Barnitz (DE)

(73) Assignee: Dräger Medizintechnik GmbH (DE)

( * ) Notice: Subject to any disclaimer, the term of this patent is extended or adjusted under 35 U.S.C. 154(b) by 127 days.

(21) Appl. No.: 09/652,104

(22) Filed: Aug. 30, 2000

(30) Foreign Application Priority Data

Mar. 21, 2000 (DE) .......................................... 100 13 960

(51) Int. Cl.[7] .................................................. F04B 35/00
(52) U.S. Cl. ........................ 417/363; 415/196; 415/206; 417/423.15; 417/423.1
(58) Field of Search ................................ 417/363, 366, 417/423.1, 423.15, 423.14; 415/119, 206

(56) References Cited

U.S. PATENT DOCUMENTS 5,140,819 A * 8/1992 Napier et al. ................ 415/119
5,161,939 A * 11/1992 Stadler ......................... 415/177
6,193,463 B1 * 2/2001 Adeff et al. ................. 415/206

FOREIGN PATENT DOCUMENTS

DE 91 04 643.2 11/1991
DE 197 14 644 C2 10/1998

OTHER PUBLICATIONS

Elselvier Science Ltd, 1995, Elselvier Science Ltd, Pumping Manual 9th Edition, 4 pages.*
Kurt Schreckling, Thomas Kamp and Dr. Jesus Artes, Feb. 21, 2002, The Engines, 5 pages.*

* cited by examiner

Primary Examiner—Charles G. Freay
Assistant Examiner—John F Belena
(74) Attorney, Agent, or Firm—McGlew and Tuttle, P.C.

(57) ABSTRACT

A radial compressor is provided for respiration purposes. The sound emissions generated by deflections and separations of the gas flow in the compressor wheel and the housing of the radial compressor and by the high-speed motor of the radial compressor are reduced. This is achieved with a specially shaped passage channel (4) for the volume flow, which exerts a stabilizing effect on the volume flow utilizing the Bernoulli principle of flow. Additional sound reduction is provided by using a separate mass (8) arranged between the motor (6) and the housing (3), which absorbs the sound energy generated by the high-speed motor (6). Also sound reduction is provided by suspending the radial compressor with membranes in a closed capsule.

20 Claims, 3 Drawing Sheets

RESPIRATOR RADIAL COMPRESSOR WITH REDUCED SOUND EMISSION

FIELD OF THE INVENTION

The present invention pertains to a radial compressor for respiration purposes with reduced sound emission.

BACKGROUND OF THE INVENTION

Radial compressors offer the possibility of achieving pressure-controlled patient respiration in both mobile devices as they are used in the area of home care and in stationary devices as they are used, e.g., in hospitals.

Small, high-speed radial compressors with low moments of inertia are used in order for the radial compressors to be able to directly follow the current pressure requirement of the patient via a change in speed.

A corresponding gas delivery means for respirators and anesthesia apparatuses in the form of a radial compressor with backwardly curved blades is described in DE 197 14 644 C2. The advantages of this radial compressor are its simple and compact design and the possibility of covering a broad speed and pressure range by means of rapid control of the electric drive motor.

The drawback was found to be the disturbing development of noise because of the structure-borne noise generated by the high-speed motor and the air-borne sound generated by deflections and the separations of the gas flow in the compressor wheel and the housing of the radial compressor.

An improvement in terms of the structure-borne noise generated by the high-speed motor is presented in DE 199 04 119 A1. This reference, assigned to the assignee of this application, is not prior art to this application. The U.S. counterpart application Ser. No. 09/354,383 is hereby incorporated by reference. The breathing gas itself is used there as a lubricant between the sliding surfaces moving in relation to one another. Due to the design of the aerodynamic plain gas bearing, the rotor and the stator are separated from one another in a completely wear-free manner, so that the noise generation is substantially reduced.

Another device for noise reduction in patient respirators is described in WO 99/22794. In this reference, the motor bringing about the delivery of gas is accommodated in an additional housing made of a sound-absorbing material.

The drawback in all the above-mentioned cases is that the reduction of the sound emission, especially of the air-borne noise, but also of the structure-borne noise, which originates from the radial compressor especially during the increase in speed, is still insufficient.

The reduction in air-borne sound has an especially good effect if it takes place directly at the source of the sound, i.e., at the radial compressor. In particular, sound reduction during the deflection of the volume flow of breathing gas being fed to the radial compressor from the direction parallel to the axis of rotation to the direction at right angles to the axis of rotation of the compressor wheel of the radial compressor offers the advantage that it can take place independently from the particular capacity coefficient, i.e., the ratio of the speed of the compressor wheel to the speed of the volume flow.

Sound reduction takes place during the deflection of the gas volume flow of breathing gas being fed to the radial compressor due to a special design of the passage opening provided for the volume flow between the compressor wheel and the housing. The compressor wheel has a ring-shaped, stretched lip arranged at the lower ends of the blades, so that an annular gap is formed between the lip at the lower ends of the blades of the compressor wheel and the housing. Through this gap a leakage flow reaches, in the opposite direction, the rest of the volume flow. The leakage flow prevents undesired separations from this volume flow. This annular gap is very small in the small radial compressors used with such respirator applications. The manufacture and adjustment are extremely complicated. On the other hand, the width of the annular gap allows only small tolerances in view of the stabilizing effect of the leakage flow. Another drawback is that the radial compressors used for respiration purposes require the frequent removal and replacement of individual components, so that it is difficult to permanently maintain the small tolerances.

SUMMARY AND OBJECTS OF THE INVENTION

The object of the present invention is therefore to provide a radial compressor that has reduced air-borne sound and requires only a small design effort.

A radial compressor is provided with a motor-driven compressor wheel rotating around an axis of rotation and a stationary housing surrounding the compressor wheel. The compressor has a volume flow, which can be fed to the axis of rotation via an intake mouth and leaves the compressor wheel at right angles to the axis of rotation. The passage opening is formed by the intake mouth. The compressor wheel and the blade ends first narrow in the direction of the volume flow being fed in and then expands.

Bernoulli's principle of flow is utilized according to the present invention in shaping the passage opening formed by the intake mouth, the compressor wheel and the housing of the radial compressor. Due to the fact that the passage opening first narrows in the direction of the volume flow being fed and then expands, the volume flow has a higher velocity in the narrowed part of the passage opening. This exerts a stabilizing effect and prevents undesired separations of the volume flow during the deflection. The advantage is, in addition, that reduced requirements are imposed on the tolerances to be maintained in the intake mouth, the compressor wheel and the housing relative to their axial and radial dimensions. The removal and replacement of individual components can thus take place in a substantially more problem-free manner.

Furthermore, it is possible to create a passage opening for the volume flow with a nearly constant change in cross section by shaping the hub of the compressor wheel, as a result of which the tendency to generate separations from the volume flow is additionally kept low. The advantages of reduced separations are, on the one hand, reduced sound emission, and, on the other hand, improved efficiency of the radial compressor. The narrowing of the passage opening according to the present invention and the subsequent expansion should be between 10% and 50% at the entry of the intake mouth, measured on the cross section of the passage opening. A lesser narrowing leads to excessively weak effects, while a greater narrowing leads to additional technical complications, namely, if a steadily sufficient volume flow is to be guaranteed for the patient respiration.

In a preferred embodiment, the passage opening has, when viewed in the direction of the volume flow being fed in, initially a circular cross section. Adjoining the narrowing, it expands between the compressor wheel and the inner wall of the housing. The diameter of the circular cross section is first 20 mm, after which it narrows continuously to 14 mm and it is 20 mm after the expansion of the passage opening, measured in the free cross section of the intake mouth.

Besides the air-borne sound caused by the deflection of the gas flow, increased propagation of structure-borne noise intensifying the noise emission is caused above all by the high-speed motor. This is caused by the imbalance and the offset of the centers of the moving parts of the motor as well as running noises of the bearings in the motor.

The high-speed motors introducing the power have been hitherto coupled with the housing of the radial compressor as softly as possible by means of elastomers. The drawback of this was found to be that the coupling is very soft for low frequencies, but it is increasingly harder for higher frequencies. The damping behavior of the coupling of the motor and compressor, via elastomers, is therefore highly frequency-dependent. Low frequencies are damped well and higher frequencies poorly. If this frequency dependence of the damping with elastomers is to be extensively eliminated by selecting very soft elastomers, which still offer sufficient damping at both low and high frequencies, problems will arise due to the inaccuracy of the positions of the components of the radial compressor in relation to one another, which are allowed to have a tolerance range of only about 0.2 mm in terms of their position in space.

Another drawback of the use of elastomers for damping the structure-borne noise occurring in radial compressors is their critical long-term behavior, which is expressed in the form of a possible flow of material and a change in viscosity.

A special embodiment with rigid coupling of the motor driving the compressor wheel of the radial compressor and the housing of the radial compressor via the intermediary of a separate mass via a spring element has proved to be advantageous for reducing the structure-borne noise occurring due to the high-speed motor. The structure-borne noise generated by the rotation of the motor is reduced now by the. vibration energy being absorbed by a sufficiently large mass, which vibrates instead of the motor and reduces the amplitude of the coupling point.

Aluminum proved to be particularly favorable for use for the separate mass, because the reduction of the structure-borne noise is additionally brought about by the material-specific internal damping of the aluminum, besides the above-mentioned effect. The internal damping structure increased energy conversion of the structure-borne sound due to the inner friction of the aluminum during vibration. Comparable advantages arise with the use of brass as the material for the separate mass. However, regardless of other material-specific properties, it is, in general, advantageous for the material used to have a high specific gravity.

The coupling of the motor and the housing of the radial compressor according to the present invention via the intermediary of a separate mass contains no elastic connections, so that the problems caused by inaccuracies in position and the critical long-term behavior of the elastomers are eliminated.

The weight of the separate mass is advantageously 1 to 4 times the weight of the motor. The separate mass is preferably coupled elastically and with low damping via a thin, metallic flange between the motor and the housing.

The weight of the separate mass is limited upward by the flange, with which the separate mass is coupled, still being able to transmit the forces that occur. High specific gravity of the separate mass is advantageous in this connection as well, because the entire separate mass is arranged as a result as close to the coupling point between the motor and the housing as possible.

In a preferred embodiment, the weight of the separate mass is 185 g, the separate mass has a cylindrical shape with an external diameter of 40 mm, an internal diameter of 24 mm and a height of 25 mm. The flange for coupling the mass has a thickness of 1.5 mm.

The use of the separate mass besides the coupling between the motor and the housing for reducing the structure-borne noise as an element of a motor temperature measring means or for better removal of the heat generated by the motor offers an additional advantage.

In an additional advantageous embodiment, a further reduction of the sound emission is achieved by the radial compressor according to the present invention being fastened by suspension in membranes and by the radial compressor according to the present invention being arranged in a closed capsule.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIENT

Figure 1:
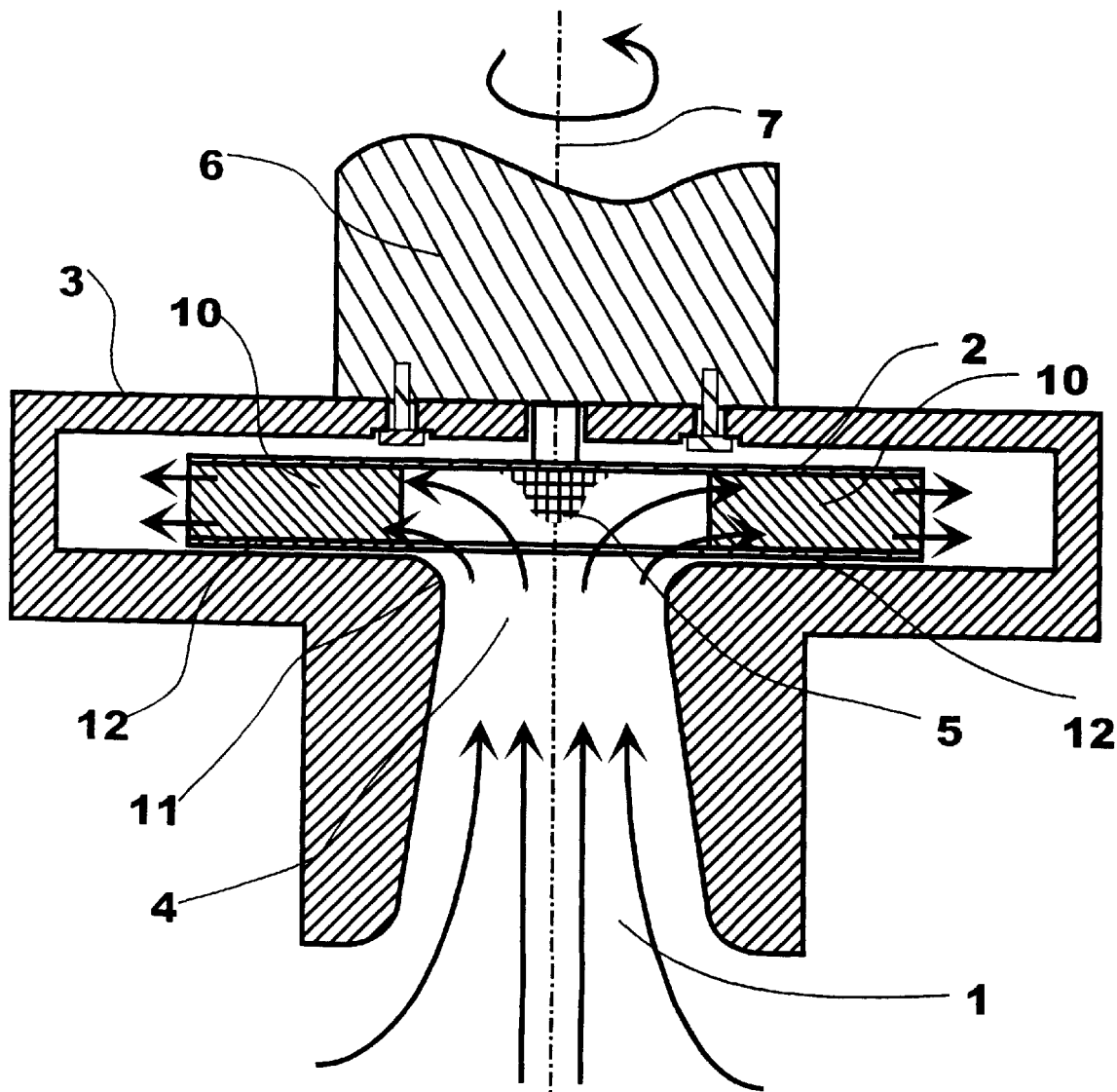
FIG. 1 is a sectional view of the design of a radial compressor according to the present invention with passage opening for the volume flow.

Referring to the drawings in particular, FIG. 1 shows the sectional view of the design of a radial compressor according to the present invention with volume flow passage opening 4, which design is symmetrical around the axis of rotation 7. The radial compressor comprises a compressor wheel 2 rotating around the axis of rotation 7, with blades 10, with blade end 12 and with a hub 5, with a stationary housing 3 surrounding the compressor wheel 2, and with an intake mouth 1, which projects therefrom and extends in parallel to the axis of rotation 7. A shaft of the motor 6 is connected to the hub 5, for rotating the compressor wheel 2 around the axis of rotation 7.

The volume flow of the gas that is compressed in the radial compressor and is subsequently fed to the patient, not shown in FIG. 1, for respiration, is indicated by arrows in FIG. 1. It enters the radial compressor through the passage opening 4, which initially narrows and then expands in an annular shape. The passage opening 4 is the channel defined by the intake mouth 1, the compressor wheel 2 and the blade ends 12, which narrows and then expands continuously. The continuous curvature at critical points of the passage opening 4, at which the volume flow is deflected without flow separation, is guaranteed especially by the hub 5, which tapers in a concave form in the direction of the axis of rotation 7, and the rounded transition 11 from the intake mouth 1 to the inner wall of the housing 3.

Figure 2:
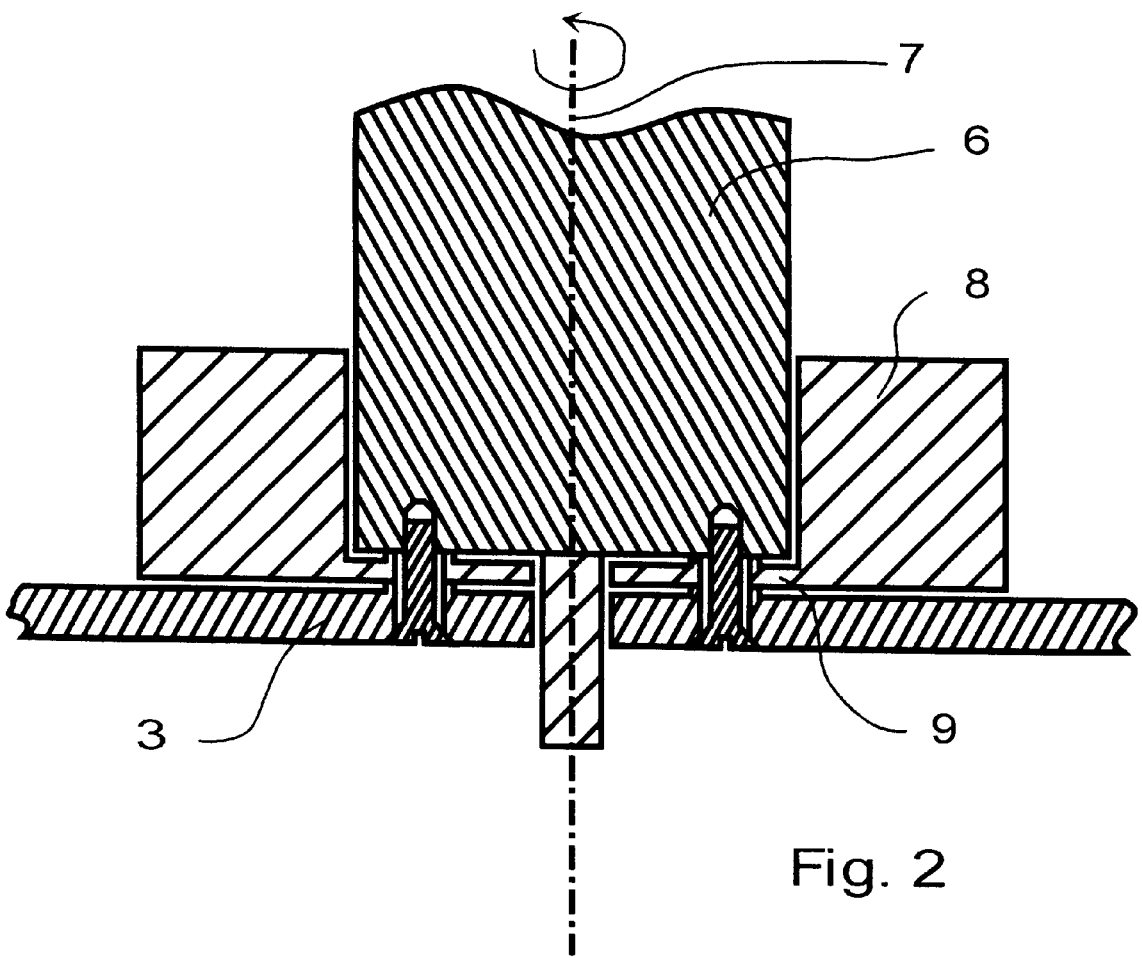
FIG. 2 is a sectional view of the motor and parts of the housing of a radial compressor according to the present invention with an intermediate separate mass.

FIG. 2 shows the motor 6 and parts of the housing 3 of a radial compressor according to the present invention with an intermediate, separate mass 8. The separate mass 8 has a metallic flange 9, with which it is rigidly inserted between the motor 6 and the housing 3 of the radial compressor and which has a weight corresponding to approx. 1.5 to 2 times the weight of the motor 6.

The arrangement according to FIG. 2 is rotationally symmetrical to the axis of rotation 7.

Figure 3:
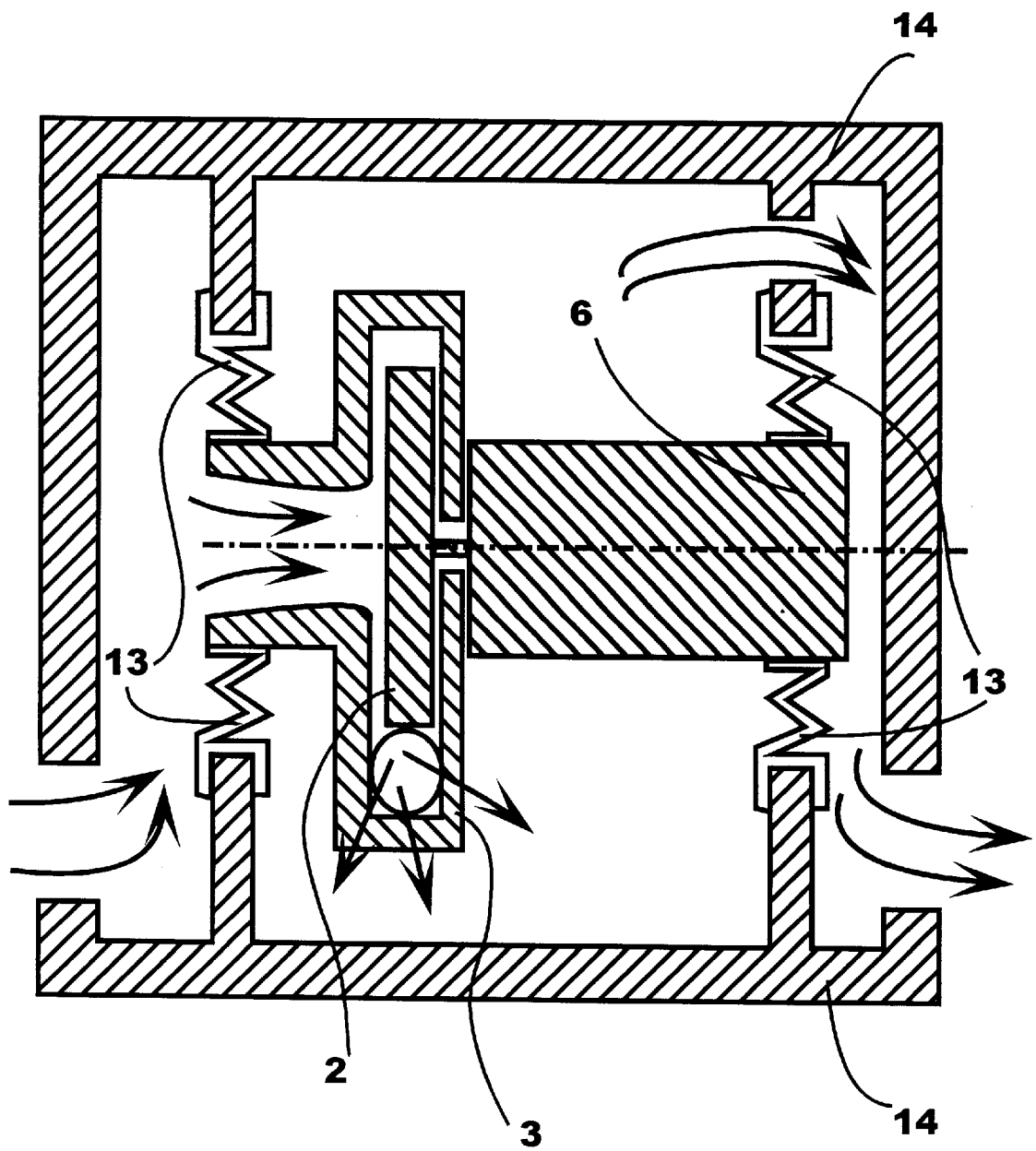
FIG. 3 is a selective view of the radial compressor in a closed capsule to the present invention with a suspension in membranes.

FIG. 3 shows the capsule 14 and the membranes 13. A sound emission lowering is achieved by the radial compressor being fastened by suspension in membranes 13 in the housing 3 or part of the housing 3. The radial compressor according to the present invention may be arranged in a closed capsule 14 formed in part by the housing 3.

While a specific embodiment of the invention has been shown and described in detail to illustrate the application of the principles of the invention, it will be understood that the invention may be embodied otherwise without departing from such principles.

What is claimed is:

1. A radial compressor, comprising:
   a motor-driven compressor wheel rotating around an axis of rotation;
   a stationary housing surrounding the compressor wheel, the housing defining a flow passage for feeding gas in a direction of the axis of rotation, the flow passage including an intake mouth, with gas leaving the compressor wheel at right angles to the axis of rotation, a passage opening of said flow passage being disposed adjacent to said intake mouth, said compressor wheel and blade ends of said compressor wheel, said passage opening narrowing in a direction of the volume flow being fed in and then expanding; and
   a separate mass, wherein said motor driving said compressor wheel is coupled to said housing with low damping via the intermediary of said separate mass.

2. A radial compressor in accordance with claim 1, wherein said compressor wheel has a hub, said hub and a transition from the intake mouth to the inner wall of the housing is shaped such that said passage opening formed between said intake mouth, said compressor wheel and said blade ends has a continuous change in cross section.

3. A radial compressor in accordance with claim 1, wherein a narrowing of said passage opening, measured on a cross-sectional area of said passage opening at an inlet of said intake mouth, is at least 10% and at most 50%.

4. A radial compressor in accordance with claim 1, wherein the material of said separate mass is aluminum.

5. A radial compressor in accordance with claim 1, wherein the material of said separate mass is brass.

6. A radial compressor in accordance with claim 1, wherein a weight of said separate mass is 1 to 4 times the weight of a mass of said motor.

7. A radial compressor in accordance with claim 1, wherein the complete radial compressor with the motor is fastened by suspension in membranes.

8. A radial compressor in accordance with claim 1, wherein the radial compressor is arranged in a closed capsule.

9. A radial compressor, comprising:
   a motor-driven compressor wheel rotating around an axis of rotation, the compressor wheel having a central intake region and a radially outward discharge;
   a stationary housing surrounding the compressor wheel, the housing having a flow passage portion adjacent to said central intake region of said compressor wheel, said flow passage portion first narrowing in a direction of the volume flow being fed in and then expanding; and
   a separate mass disposed between said housing and said motor, wherein said motor is coupled to said housing with low damping via the intermediary of said separate mass.

10. A radial compressor in accordance with claim 9, wherein said passage portion has a continuous change in cross section.

11. A radial compressor in accordance with claim 9, wherein a narrowing of said passage portion, measured on a cross-sectional area of said passage portion at an inlet of an intake mouth, is at least 10% and at most 50%.

12. A radial compressor in accordance with claim 10, wherein the material of said separate mass is aluminum.

13. A radial compressor in accordance with claim 10, wherein the material of said separate mass is brass.

14. A radial compressor in accordance with claim 10, wherein a weight of said separate mass is 1 to 4 times the weight of a mass of said motor.

15. A radial compressor in accordance with claim 10, wherein the complete radial compressor with the motor is fastened by suspension in membranes.

16. A radial compressor in accordance with claim 10, wherein the radial compressor is arranged in a closed capsule.

17. A radial compressor, comprising:
   a motor-driven compressor wheel rotating around an axis of rotation, the compressor wheel having a central intake region and a radially outward discharge;
   a stationary housing surrounding the compressor wheel, the housing having a flow passage portion adjacent to said central intake region of said compressor wheel, said flow passage portion first narrowing in a direction of the volume flow being fed in and then expanding;
   a separate mass having a metallic flange coupled elastically and with low damping between said housing and said motor.

18. A radial compressor in accordance with claim 17, wherein a weight of said separate mass is 1 to 4 times the weight of a mass of said motor.

19. A radial compressor in accordance with claim 17, wherein the material of said separate mass is one of aluminum and brass.

20. A radial compressor in accordance with claim 17, wherein the flow passage portion cooperates with a channel defined by the intake mouth of the compressor wheel and the blade ends of the compressor wheel narrow and then expand.

* * * * *